(12) United States Patent
Ross

(10) Patent No.: US 7,806,527 B2
(45) Date of Patent: Oct. 5, 2010

(54) ELECTROMAGNETIC BEAM DETECTION SYSTEM

(76) Inventor: Colin A. Ross, 2743 Brookside La., McKinney, TX (US) 75070

( * ) Notice: Subject to any disclaimer, the term of this patent is extended or adjusted under 35 U.S.C. 154(b) by 314 days.

(21) Appl. No.: 11/839,594

(22) Filed: Aug. 16, 2007

(65) Prior Publication Data

US 2009/0046246 A1 Feb. 19, 2009

(51) Int. Cl.
 *A61B 3/00* (2006.01)
(52) U.S. Cl. ..................................................... 351/200
(58) Field of Classification Search ................. 351/200; 340/551, 572.2
 See application file for complete search history.

(56) References Cited

U.S. PATENT DOCUMENTS

| | | | | |
|---|---|---|---|---|
| 4,863,259 | A * | 9/1989 | Schneider et al. | 351/210 |
| 5,861,936 | A * | 1/1999 | Sorensen | 351/200 |
| 7,540,613 | B2 * | 6/2009 | Severns | 351/205 |
| 2002/0103439 | A1 | 8/2002 | Zeng et al. | |
| 2003/0223039 | A1 | 12/2003 | Thomas | |
| 2004/0039297 | A1 * | 2/2004 | Abreu | 600/558 |
| 2004/0061834 | A1 | 4/2004 | Zhou et al. | |
| 2006/0052709 | A1 | 3/2006 | DeBaryshe et al. | |
| 2006/0135880 | A1 * | 6/2006 | Sarkela | 600/544 |

OTHER PUBLICATIONS

International Search Report, Jan. 15, 2009.
Harland, C.J. et al.; "Electric potential probes-new directions in the remote sensing of the human body"; Measurement Science and Technology, 13 (2002) pp. 163-169; Institute of Physics Publishing Ltd., UK.
Myers, Hal K.; "Recent Advances in EMG Monitoring"; Jun. 1989 (updated May 2000) Conference of Physiotherapists of Quebec; www.thoughttechnology.com/hal.htm.
Lee, Jaime M. et al.; "Evaluating a Capacitively Coupled, Noncontact Electrode for ECG Monitoring"; Dec. 1, 2005; Sensors, Questex Media Group, Newton MA, mil.sensorsmag.com.
Quasar; "Noninvasive Biosensing Systems"; Quantum Applied Science and Research, Inc., San Diego CA.
Thought Technology; ProComp Infiniti data sheet with specifications; 2006, Thought Technology Ltd., Quebec, Canada http://www.thoughttechnology.com/proinf.htm , http://www.thoughttechnology.com/pdf/specs/ProComp%20Infiniti%20Encoder.pdf.
Electrode Store, "EEG Electrodes"; 2007, The Electrode Store, Enumclaw, WA http://www.electrodestore.com/EEG/EEG.lasso?ran=38FB8D7A&S=10&T=37.
Wikipeia, "Mu-metal"; 2007, Wikimedia Foundation, Inc., Florida USA http://en.wikipedia.org/wiki/Mu-metal.

* cited by examiner

*Primary Examiner*—Ricky L Mack
*Assistant Examiner*—Mahidere S Sahle
(74) *Attorney, Agent, or Firm*—Carr LLP

(57) ABSTRACT

The present invention provides for a Line of Sight (LOS) electromagnetic beam (EM) detection system configured with an enclosure, a detection device, a processing device, a storage device, and a communication device. The enclosure may or may not be electromagnetically shielded from the surrounding environment. The enclosure may contain one or more detection devices and one or more portals configured for a user to look through. The detection devices may be a non-contacting, active-dry electroencephalogram (EEG) electrode or a high input impedance EEG electrode. The processing device may be a specifically programmed general purpose computer. The communication device may be auditory and/or visual. The storage device may store signals from the detection device for later analysis and statistical manipulation. In some embodiments, the LOS detection system may be used as a switch responding to interaction with a LOS beam emanating from an ocular cavity.

22 Claims, 4 Drawing Sheets

FIG. 1
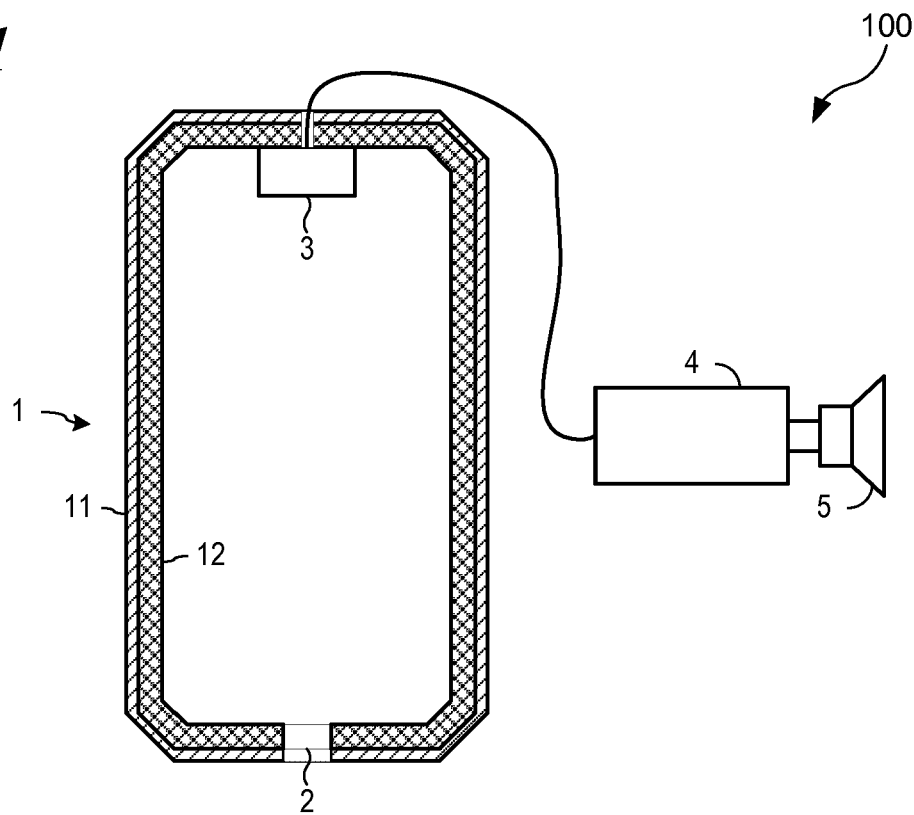
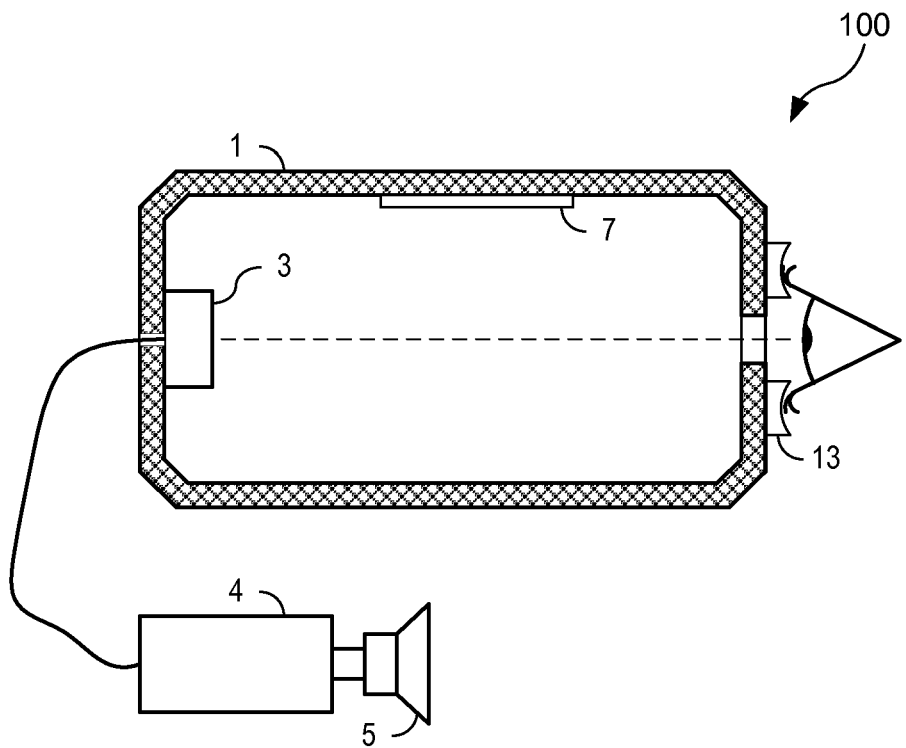
FIG. 2

ELECTROMAGNETIC BEAM DETECTION SYSTEM

BACKGROUND OF THE INVENTION

1. Field of the Invention

The present invention relates to an electromagnetic detection system for the non-contacting detection of electromagnetic fields emanating from a living organism and, more particularly, to the detection of electromagnetic fields emanating from an ocular cavity.

2. Description of the Related Art

All biological systems generate electromagnetic fields (EMF) and these fields interact with and are affected by the magnetic field surrounding the earth as well as other sources of EMF such as solar flares. The human body in particular generates a relatively complex electromagnetic field. Measuring, sensing, and detecting the electromagnetic field may provide important information for understanding the inner workings and the treatment of the human body. There currently exist known methods of measuring the electromagnetic field of a body. The electromagnetic field generated by the brain, for example, can be measured with a highly sensitive instrument such as a Superconducting Quantum Interference Device (SQUID) magnetometer. However, since the magnetic field generated by the brain is on the order of roughly one billion times weaker than the main magnetic field of the earth, most SQUID magnetometers are typically housed in magnetically insulated rooms in order to eliminate the background noise that would otherwise overwhelm the signal from the brain. Such full-size rooms can cost approximately $250,000 to construct and a SQUID magnetometer capable of taking a full brain map costs about $2 million.

A less costly way to measure the electrical field generated by the brain is through the use of a contacting electroencephalogram (EEG) system. A simple EEG software program and the necessary leads and electrodes can be purchased for about $1,200 and run on a laptop computer. A system such as this is commonly used during biofeedback treatment by psychologists. Biofeedback is the process of monitoring a physiological signal, and amplifying, conditioning, and displaying the signal to the monitored subject so that he or she can observe small changes in the signal. Gradually, through trial and error, the monitored subject may learn to affect certain biological or physiological processes by associating certain actions with the subsequent changes in the monitored signal.

Additionally, in some situations the measurement of electric fields produced by the body may be useful in identifying certain medical conditions or in the development of medical treatments. For example, a typical application involves the measurement of the electrical field of the heart through the use of a contacting electrocardiogram (ECG or EKG). The printout of the measurement may be used in making a number of different diagnoses, including the likelihood of a heart attack, and the identification of abnormal electrical conduction within the heart, among others. Another application involves the measurement of an electromagnetic beam emanating from the ocular region of a human head. This electromagnetic beam is essentially a line of sight (LOS) beam able to focus an electromagnetic field on whatever the person is looking at. However, traditional methods of attaching an electrode to contact the surface of the skin in order to measure the electromagnetic field are difficult due to the sensitive nature of the eyes. Therefore, there exists a need for a low cost, non-contacting measurement device configured to detect and respond to the LOS beam.

SUMMARY OF THE INVENTION

The present invention provides a system for detecting an electromagnetic beam. The system may comprise an enclosure configured to facilitate visual access for an eye and containing a detecting device comprising at least one electrode. The system may further comprise a processing device configured to receive an output from the detecting device. Additionally, the system may comprise a communication device configured to provide feedback communication corresponding to the output from the detecting device.

BRIEF DESCRIPTION OF THE DRAWINGS

For a more complete understanding of the present invention and the advantages thereof, reference is now made to the following Detailed Description taken in conjunction with the accompanying drawings, in which:

FIG. 1 illustrates an embodiment of an electromagnetic LOS beam detection system configured according to the present invention;

FIG. 2 illustrates an application of the electromagnetic LOS beam detection system of FIG. 1;

DETAILED DESCRIPTION

Figure 3:
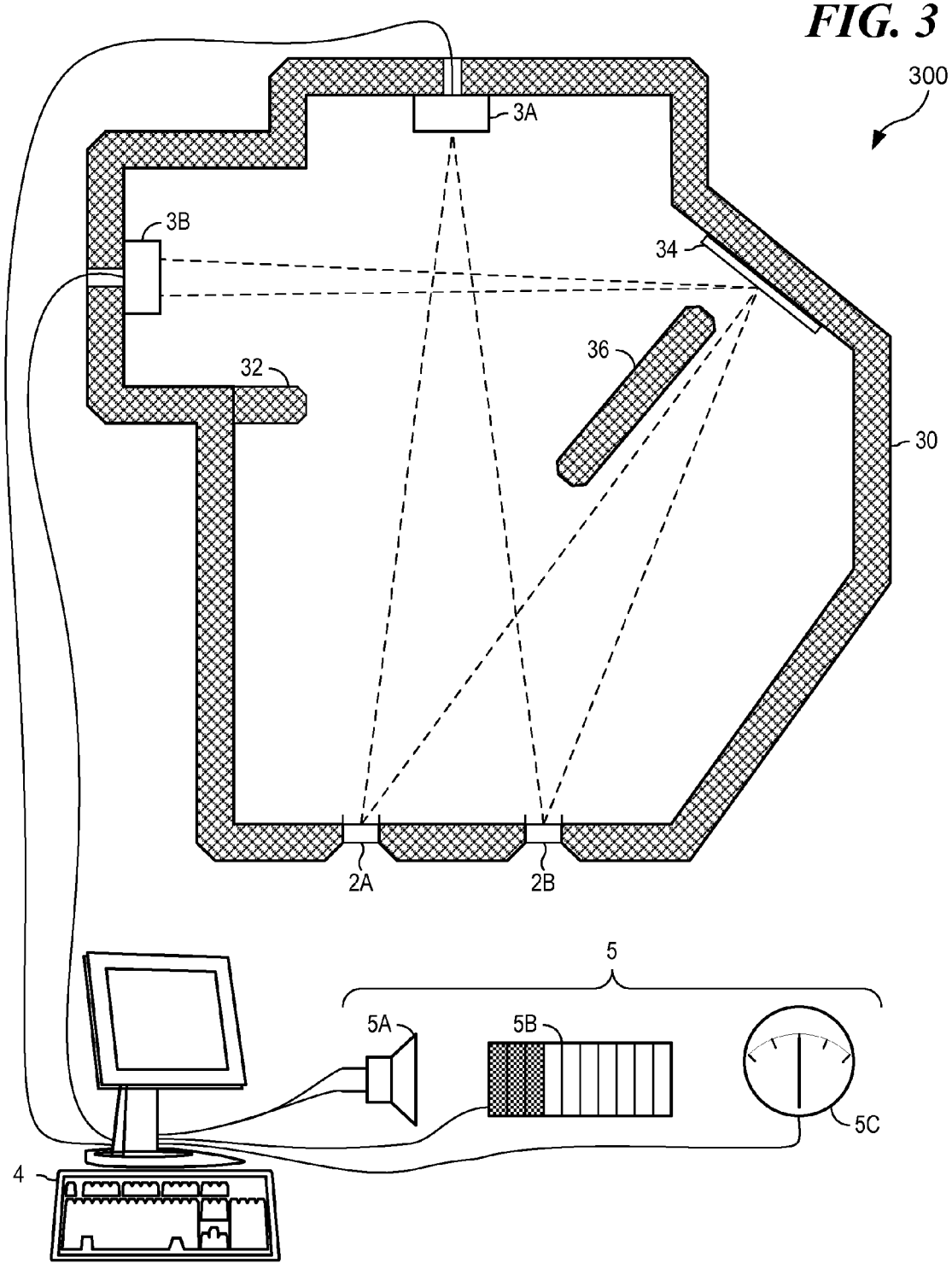
FIG. 3 illustrates another embodiment of an electromagnetic LOS beam detection system configured according to the present invention.

In the following discussion, numerous specific details are set forth to provide a thorough understanding of the present invention. However, those skilled in the art will appreciate that the present invention may be practiced without such specific details. In other instances, well-known elements have been illustrated in schematic or block diagram form in order not to obscure the present invention in unnecessary detail. Additionally, for the most part, details concerning network communications, electromagnetic signaling techniques, and the like, have been omitted inasmuch as such details are not considered necessary to obtain a complete understanding of the present invention, and are considered to be within the understanding of persons of ordinary skill in the relevant art.

Turning now to FIG. 1, the reference numeral 100 generally indicates an illustrative example of an embodiment of an electromagnetic line of sight (LOS) beam detection system 100 configured according to at least some aspects of the current invention. The LOS beam detection system 100 may comprise an enclosure 1, detection device 3, processing device 4, and a feedback device 5. The components of the LOS beam detection system 100 will be described in more detail in the following.

The enclosure 1 may completely surround a detection device 3 and may be electromagnetically (EM) shielded. An EM shielded enclosure 1 may facilitate the filtering out or elimination of background electromagnetic interference or noise typically present in the environment. The enclosure 1 may be configured in a variety of shapes and sizes, not limited to the illustrative example shown. In some embodiments, the enclosure 1 may be in the form of a hand-held device approximately the size and shape of a pair of binoculars, among others. As shown in FIG. 1, a relatively simple enclosure approximately in the shape of a sealed cylinder, among others, may be used for the enclosure 1.

An EM shielded enclosure 1 may comprise a central core structure 12 overlaid with an electromagnetic shielding material 11 or in some cases, may be directly formed from the shielding material 11. The central core structure 12 may be formed from any of a wide variety of lightweight and/or low cost materials, such as polypropylene, aluminum, cardboard or other compressed fiber material, and wood, among others. Some examples of shielding material 11 include mu-metal, a nickel-iron alloy comprising approximately 75% nickel, 15% iron, plus copper and molybdenum, among others. Mu-metal has a very high magnetic permeability and may be very effective at screening static or low-frequency magnetic fields. Other materials that may exhibit similar properties include supermalloy, supermumetal, nilomag, sanbold, and Mo-permalloy, among others. The examples listed are not intended to form an exhaustive list but are instead intended to illustrate a representative selection from a wide variety of appropriate materials.

The enclosure 1 may comprise one or more portals 2 (i.e., openings) configured to provide visual access for a corresponding number of eyes. In the embodiment shown in FIG. 1, a single portal 1 may be provided for a single eye of a monitored subject. In other embodiments, two portals may be provided for both eyes of a single monitored subject. With larger devices, 2 or more portals may be provided for two or more monitored subjects simultaneously undergoing monitoring. The portal 2 may be covered with a transparent member such as glass, plastic, acrylic, or other non-electromagnetic shielding material, among others, so as to completely enclose the interior of the enclosure 1. In some cases, the portal 2 may be open, eliminating any obstruction between the LOS beam and the detection device 3. The exterior surface surrounding the portal 2 may be configured to comfortably accommodate the surrounding structure of an eye, including but not limited to, a resilient interface 13 (FIG. 2) such as a foam surround or camera type of rubber eyepiece for example, among others. The resilient interface 13 may also comprise EM shielding material to reduce or further inhibit the passage of electromagnetic background noise or interference into the interior chamber of the enclosure 1.

The detection device 3 may be a non-contacting, active-dry electroencephalogram (EEG) electrode configured to measure electrical signals from the brain. Conventional EEG electrodes may have input impedances up to an order of about $10^6 \Omega$ to $10^7 \Omega$. A detection device 3 comprising conventional EEG electrodes may require EM shielding surrounding the enclosure 1 to reduce interference from surrounding electromagnetic and other noise. The length of the enclosure 1 may be designed to correspond with the ability of the EEG electrode to remotely sense the LOS beam. The non-contacting, active-dry EEG electrode may comprise tin, gold, silver, or other appropriate materials, in addition to combinations of these materials, configured as discs.

Alternatively, the detection device 3 may be a high (or ultra-high) impedance EEG electrode. A high impedance EEG electrode may have an input impedance from about $10^7 \Omega$ up to approximately $10^{15} \Omega$. The noise floors of high impedance EEG electrodes may be on the order of approximately 70 $\eta V\, Hz^{-1/2}$ at 1 Hz. Due at least in part to the low noise levels achievable with high impedance EEG electrodes, a LOS beam detection system 100 may require only modest, if any at all, electromagnetic shielding for the enclosure 1, even at the highest levels of sensitivity, when the detection device 3 comprises one or more high impedance EEG electrodes. An optimization between the cost of the high impedance EEG electrodes and the cost of the electromagnetic shielding may drive the overall configuration of the LOS beam detection system 100. As with the other EEG electrodes comprising the detection device 3, the length of the enclosure 1 may be designed to correspond with the ability of the high impedance EEG electrode (or other embodiment of the detection device 3) to remotely sense the LOS beam.

The detection device 3 may be coupled with a processing device 4. The processing device 4 may comprise a specifically programmed general purpose micro-processor, a purpose built device with application specific instruction code, or a combination of various components working together as a system, among other embodiments. For example, a commercially available multi-channel, multi-modality encoder may be connected through a USB port to a general purpose computer running appropriate software. The computer may receive the signal and amplify or otherwise convert the signal into a communicative feedback. The communicative feedback may comprise a visual display such as illuminating various amounts and/or colors of lights, graphs, and shapes, among others. Alternatively, or in addition to the visual display, the communicative feedback may comprise an audio component, such as various frequencies of tone, various frequencies or intervals of tonal bursts (e.g., such as in a traditional Geiger counter, etc.), and/or synthesized speech reacting to the detected LOS beam, among others. The communicative feedback may be via the processing device 4 (e.g., through the display or speakers typically integrated with a general processing computer), or via external devices (such as a stand alone communication device 5) driven by or coupled to the processing device 4. In all communications between various components, the connections may either be hardwired, wireless (e.g., Bluetooth®, Wi-Fi™), or a combination of various transmission methods and systems, among others.

A communication device 5 may be coupled to the processing device 4. The communication device 5 is shown as a speaker only for the purposes of illustration. Many forms and methods of communicating the strength of the feedback signal from the detection device 3 may be used in place of the speaker shown as a communication device 5. One or more speakers or a more ergonomic form of speaker such as headphones, ear plugs, etc., may be used as an embodiment of the communication device 5. The communication method described in this illustrative embodiment may involve some form of auditory communication so that a monitored subject may not have to avert their eyes from the detection device 3 in order to receive the communicative feedback.

Turning now to FIG. 2, a method for using the LOS beam detection system 100 may be as follows. A LOS beam detection system 100 may be configured as described above, comprising an enclosure 1, a detection device 3, a processing device 4, and a communication device 5. In certain illustrative embodiments, the interior of the enclosure 1 may contain an illuminating device 7 configured to facilitate the visual detection of detection device 3 during use of the LOS beam detection system 100. Alternatively, or in addition to the illuminating device 7, at least a portion of the enclosure 1 may comprise a transparent or semi-transparent section enabling visual communication with the detection device 3 contained within the enclosure 1.

The subject may place their eye proximate to the portal 2 such that there may be a substantially direct line of sight communication between the detection device 3 and their eye (shown by a broken line). For example, the subject may place at least a portion of the area surrounding their eye directly against the resilient interface 13. The processing device 4 may process the signal from the detection device 3 and may provide a processed signal to the communication device 5. The subject may then alter physiological and/or mental aspects of their body and concentration in an attempt to manipulate the signal to a maximum level. Such alterations may include increasing or decreasing focus on the detection device 3, varying concentration efforts and levels, and relaxing or tensing the musculature surrounding the eye, among other techniques.

Another form of use may involve the monitored subject alternating between directly looking at the detection device 3 and not looking at the detection device 3. Not looking at the detection device 3 may involve altering the line of sight to one side or another of the detection device 3 and/or closing the eye proximate to the portal. In some cases, both looking to one side and closing the eye may be used. The subject may try to alter the communicative feedback from the communication device 5 through a range of on (e.g., some auditory feedback) when looking at the detection device 3, to off when not looking at the detection device 3. The LOS beam detection system 100 may also be used as a passive monitoring system for acquiring data regarding the electromagnetic waves traveling through an ocular region of the head.

Another Embodiment

Referring now to FIG. 3, the reference numeral 300 generally indicates another illustrative embodiment of the LOS beam detection system 300 configured according to at least some aspects of the present invention. In this figure, similar components may be given the same reference numbers and a detailed description of these components may not be repeated. The LOS beam detection system 300 may comprise an enclosure 30, a first and second portal 2A and 2B, a first and second detection device 3A and 3B, a reflector member 34, a processing device 4, and a communication device 5 shown a speaker 5A, illuminated bar graph 5B, and a meter 5C. The various components of the LOS beam detection system 300 will be described in greater detail below.

The enclosure 30 of the LOS beam detection system 300 may be configured to accommodate a first and second portal 2A and 2B, for each eye of a single monitored subject for example. In some applications, two monitored subjects may each use one of the first and second portals 2A and 2B. However, although two portals 2A and 2B are shown in this illustrative embodiment, the current invention may not be limited to this configuration. One portal or three or more portals may be used with the enclosure 30. As with the previously described portal 2, the first and second portals 2A and 2B may be configured to comfortably accommodate two eyes of a single subject. In some embodiments, the first and second portals 2A and 2B may be adjustable (e.g., towards and away from one another, an adjustment system is not shown in this figure) in order to adapt the LOS beam detection system 300 to a wide variety of ages and body types of individual subjects.

As seen in FIG. 3, the enclosure 30 may also be configured to accommodate two detection devices, such as a first detection device 3A and a second detection device 3B. In this illustrative embodiment, the first detection device 3A may be along a line of sight for the first and second portals 2A and 2B. However, the second detection device 3B may be obstructed from a direct line of sight via the first and second portals 2A and 2B. The obstruction for the second detection device 3B may be due to a configuration of the enclosure 30 (e.g., locating the second detection device 3B within a bottomed cylindrical cavity or around a bend in a wall for example, among others), or the obstruction may be due to secondary feature such as an internal wall 32 or some other form of electromagnetic shielding for example. As shown, the second detection device 3B may be at an angle to the first detection device 3A.

In order to facilitate a line of sight communication between the first and second portals 2A and 2B and the second detection device 3B, the enclosure 30 may contain a reflective member 34 positioned at an angle to the portals and the second detection device 3B. The reflective member 34 may comprise a optical and/or electromagnetic reflective material, among others, enabling the portals 2A and 2B to have a visual and/or electromagnetic beam direct line of sight communication with the second detection device 3B. For example, some polished metals may provide both forms of reflection for the reflective member 34. In some embodiments, a secondary internal wall 36 or more may be provided within the enclosure 30 in order to prevent cross contamination of the first and second detection devices 3A and 3B (i.e., to ensure primary detection by the first detection device 3A substantially when looking at the first detection device 3A, and primary detection by the second detection device 3B substantially when looking at the second detection device 3B).

As with the previous enclosure 1, the enclosure 30 of the LOS beam detection system 300 may be electromagnetically shielded depending at least in part upon the amount of surrounding environmental electrical noise and/or the input impedance level of the electrodes comprising the first and second detection devices 3A and 3B. The other details and materials appropriate for the enclosure 1 may be applied for the enclosure 30.

The first and second detection devices 3A and 3B may be communicatively coupled with a processing device 4 that is in turn communicatively coupled with one or more communication devices 5. As shown in this illustrative embodiment, examples of the communication devices 5 may include one or more speakers 5A, one or more illuminated bar graphs 5B, and one or more meters 5C, among others. The bar graphs 5B and the meters 5C may be stand alone components coupled to the processing device 4, or they may be virtual components visually displayed on a monitor. There may be a single communicative device 5 for each of the detection devices 3A and 3B (e.g., using separate frequency tones with a variable volume level for indicating the strength and identity of a signal from the detection devices 3A and 3B). However, a separate set of communication devices 5 may be provided for each of the detection devices 3A and 3B. In this case, each of the detection devices 3A and 3B may be individually monitored by a subject and/or a technician.

The LOS beam detection system 300 may be used to detect the strength and application of a reflected LOS beam. A subject may initially focus on the first detection device 3A and then alternate by focusing on the second detection device 3B via the reflective member 34. By receiving the communication feedback from the communication devices 5, a monitored subject may identify which detection device is receiving the LOS beam and attempt to alter the strength of the LOS beam. After a number of monitoring sessions with the first detection device 3A are recorded, such as in an electronic file or database of the processing device 4, the subject may perform and record a number of monitoring sessions with the second detection device 3B. Subsequently, statistical analysis may indicate the relative strength of a reflected LOS beam as compared to a direct LOS beam, among others.

Another Embodiment

Figure 4:
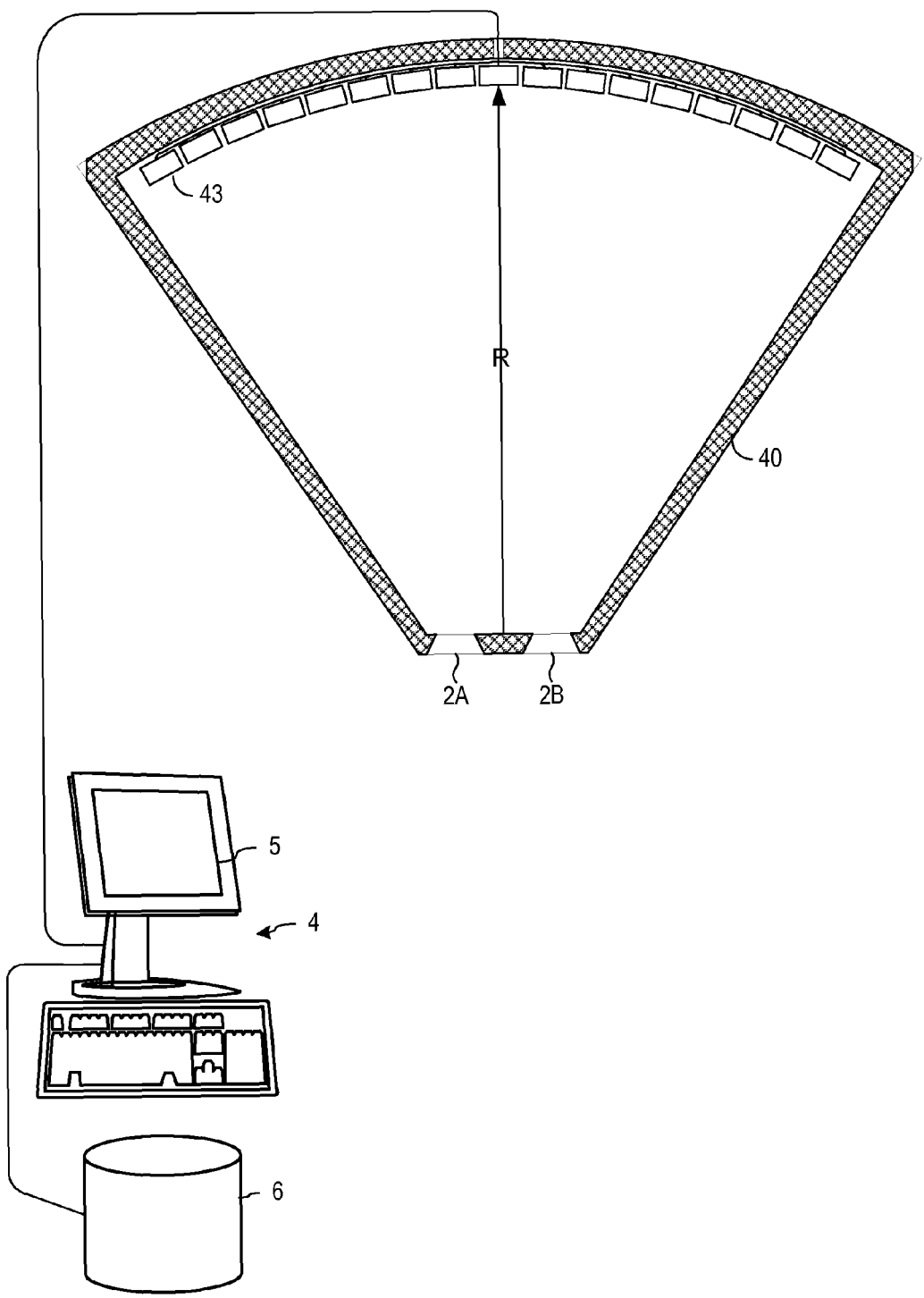
FIG. 4 illustrates another embodiment of an electromagnetic LOS beam detection system configured according to the present invention.

Turning now to FIG. 4, the reference numeral 400 generally indicates another illustrative embodiment of the LOS beam detection system 400 configured according to at least some aspects of the present invention. In this figure, similar components may be given the same reference numbers and a detailed description of these components may not be repeated. The LOS beam detection system 400 may comprise an enclosure 40, a first and second portal 2A and 2B, a plurality of detection devices 43, a processing device 4, a communication device 5, and a storage device 6. The various components of the LOS beam detection system 400 will be described in greater detail below.

In this illustrative embodiment of the present invention, a plurality of detection devices 43 is contained within an enclosure 40. The plurality of detection devices 43 may preferably be located substantially equidistantly from the first and second portals 2A and 2B, for example, such as along a substantially constant radius from a center point between the first and second portals 2A and 2B (as shown by the radius R). The plurality of detection devices 43 are shown along a single row for the purposes of illustration only. The arrangement of the plurality of detection devices 43 may be regular or irregular, in one, two, or three dimensions.

The plurality of detection devices may be coupled to a processing device 4 integrated with a communication device 5, for example. The communicative feedback for the plurality of detection devices 43 may comprise a one or two dimensional image composed of variable colors of light showing the intensity of an individual signal at a location on a monitor corresponding to the location within the enclosure 40 of the particular detection device of the plurality of detection devices 43. Video communication may be the preferred way to communicate the plurality of signal streams to the subject and/or an operator/technician. However, auditory communication may still provide information including the average intensity of the LOS beam (e.g., a volume level corresponding to the highest signal strength) or the focus of the LOS beam (e.g., a variable frequency corresponding to a ratio of the average number of detection devices indicating the presence of a signal versus the total number of the plurality of detection devices). Alternatively, the communicative feedback of the plurality of detection devices 43 may track the LOS beam as a subject looks over the plurality of detection devices 43. For example, the communicative signal may track as the subject looks from side to side within the enclosure 40 or as the subject attempts to vary the focus of the LOS beam.

The processing device 4 may be coupled to an internal and/or external storage device 6, such as an electromagnetic, optical, flash, or virtual storage device (i.e., storage across various sites on the Internet), among others. The signals from the plurality of detection devices 43 may be stored for later retrieval and statistical processing and analysis, as well as assisting medical professionals in the monitoring and diagnosis of various illnesses and treatments.

Another Embodiment

Figure 5A:
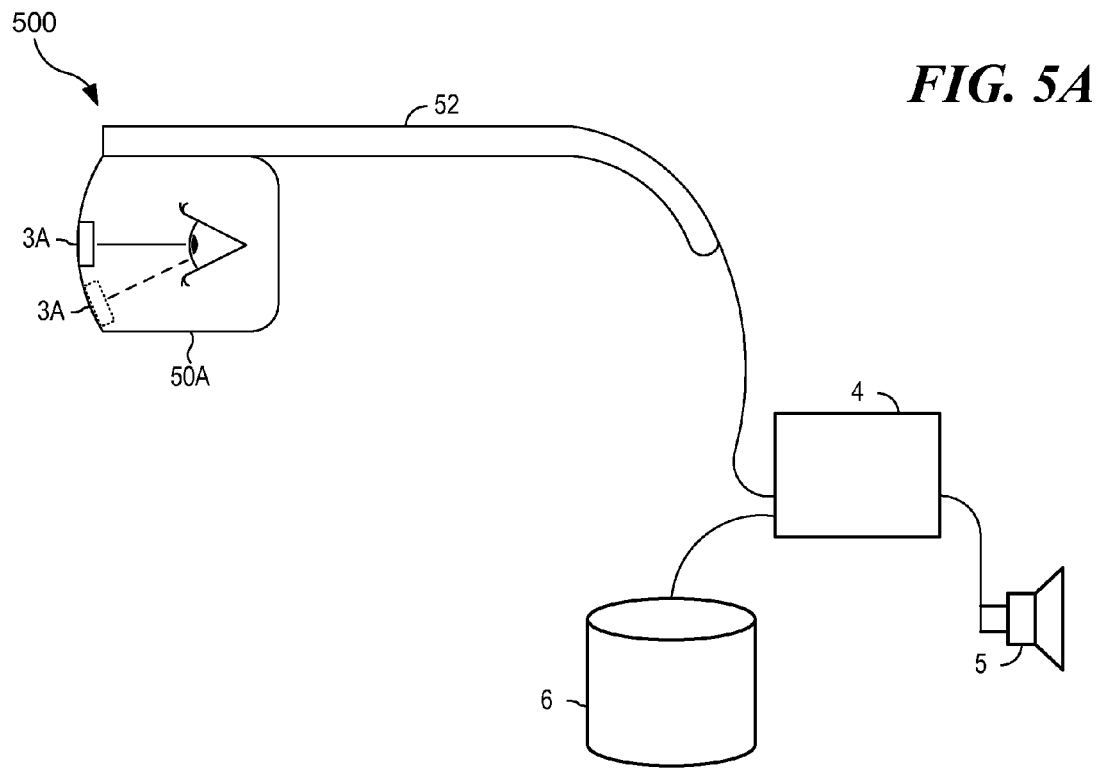
FIG. 5A illustrates a side view of another embodiment of an electromagnetic LOS beam detection system configured according to the present invention.
Figure 5B:
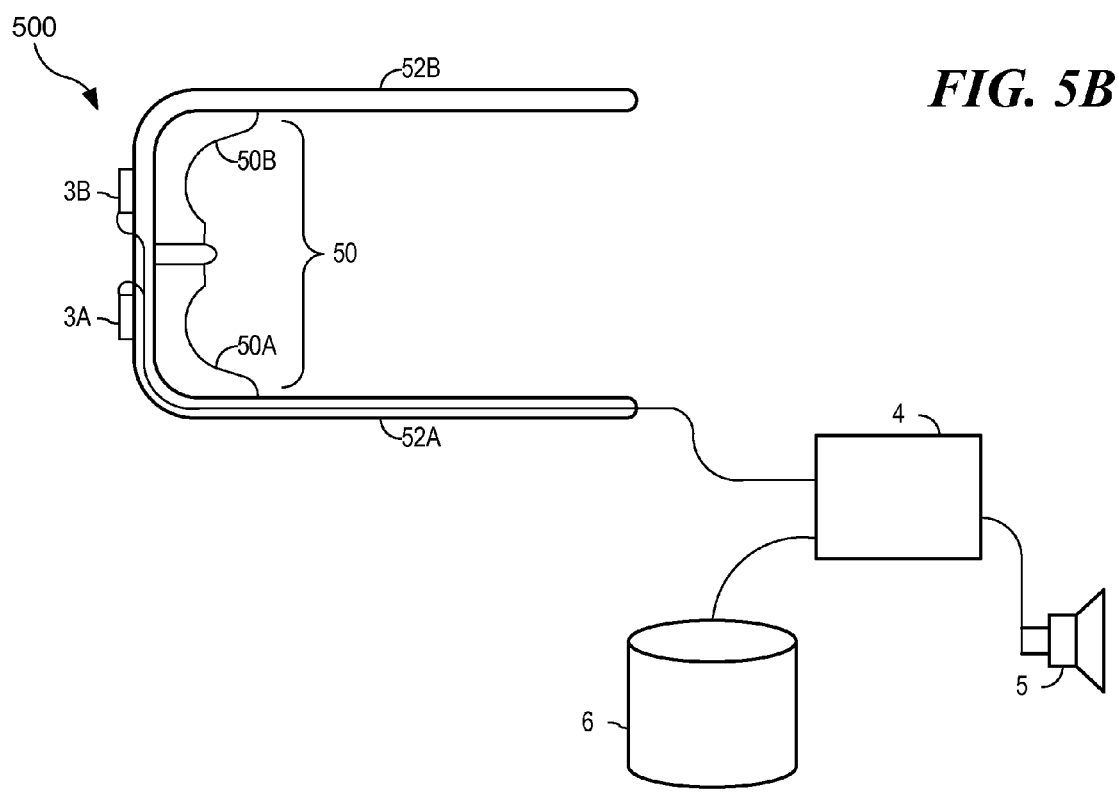
FIG. 5B illustrates a top view of the embodiment of FIG. 5A.

Referring now to FIGS. 5A and 5B, the reference numeral 500 generally indicates another illustrative embodiment of the LOS beam detection system 500 configured according to at least some aspects of the present invention. In this figure, similar components may be given the same reference numbers and a detailed description of these components may not be repeated. The LOS beam detection system 500 may comprise an enclosure 50 comprising first and second enclosures 50A and 50B (only 50A can be seen in FIG. 5A), an attachment member 52, detection devices 3 comprising first and second detection devices 3A and 3B (only 3A can be seen in FIG. 5A), a processing device 4, a communicative device 5, and a storage device 6. The various components of the LOS beam detection system 500 will be described in greater detail below.

The LOS beam detection system 500 shown in the figures may be substantially configured in the form of a pair of glasses or goggles. Since both sides of a pair of glasses are substantially symmetrical, only one side needs to be described in detail. The first enclosure 50A may fit around an eye in a manner similar to the way one side of a pair of waterproof goggles fits around an eye (e.g., forming a sealed environment within the goggles). There may not be a dedicated portal in this configuration because the first enclosure 50A may be open on one side. The eye and surrounding tissue may form the final wall of the first enclosure 50A. As with the previous illustrative embodiments, the first enclosure 50A may be electromagnetically shielded to prevent electrical noise and interference from disrupting or altering the detection signal from the first detection device 3A. In some embodiments, the first enclosure 50A may be transparent to allow the subject to visibly interact with their surroundings during the monitoring processes. In this case, a first detection device 3A with a high input impedance may be used.

The first detection device 3A may be located at any location on or within the first enclosure 50A. Preferably, the first detection device 3A may be located directly in the line of sight of a subject when the subject is looking straight ahead (e.g., indicated by the solid lines in FIG. 5A). However, in some embodiments the first detection device 3A may be located to one side or another of the first enclosure 50A (e.g., a position not normally in the line of sight, indicated by the broken lines in FIG. 5A). The LOS beam detection system 500 may function in this configuration as a switch, in which the subject may signal a change in state by looking off to the side, directly at the first detection device 3A. Whereas, during normal interaction, the subject may be able to substantially look around without triggering the first detection device 3A.

The first detection device 3A may be coupled to a processing device 4. The processing device may be internally or externally integrated with a communication device 5 and/or a storage device 6. Communicative feedback interaction and data processing and storage may be the same or similar to the previously discussed embodiments. The LOS beam detection system 500 may offer an advantage in that the detection devices 3 may be placed relatively close to the surface of the ocular area, potentially increasing the strength of the LOS beam received by each of the detection devices 3. In addition, the LOS beam detection system 500 may be worn relatively unobtrusively and conveniently, thereby permitting the monitoring and/or signaling via the detection devices 3 in a wide variety of environments and situations.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure. In some instances, some features of the present invention may be employed without a corresponding use of the other features. Many such variations and modifications may be considered desirable by those skilled in the art based upon a review of the foregoing description of preferred embodiments. Accordingly, it is appropriate that the appended claims be construed broadly and in a manner consistent with the scope of the invention.

The invention claimed is:

1. A system for detecting an electromagnetic beam comprising:
   an enclosure configured to facilitate visual access for an eye of a body and containing a detecting device comprising at least one electrode configured to produce an output corresponding to an electromagnetic field produced by the body and emanating from the eye of the body;
   wherein the detecting device is a non-contacting electrode, wherein the non-contacting electrode detects the electromagnetic field without making substantial contact with a surface of the body;
   a processing device configured to receive the output from the detecting device; and
   a communication device configured to provide feedback communication corresponding to the output from the detecting device.

2. The system of claim 1 further comprising electromagnetic shielding for the enclosure.

3. The system of claim 1, wherein the at least one electrode is a high input impedance electrode with an input impedance in the range of $10^7\Omega$ to $10^{15}\Omega$.

4. The system of claim 1 further comprising at least one speaker for the communication device.

5. The system of claim 4, wherein the at least one speaker comprises a pair of headphones.

6. The system of claim 1 further comprising a visual display device for the communication device.

7. The system of claim 6, wherein the visual display device comprises an illuminated bar graph.

8. The system of claim 1, wherein the enclosure comprises substantially a bottomed cylinder adapted to conform to an area surrounding the eye.

9. The system of claim 1, wherein the enclosure comprises a container adapted to conform to an area surrounding the eye.

10. The system of claim 1, wherein the at least one electrode comprises a plurality of electrodes.

11. The system of claim 10, wherein the plurality of electrodes are provided substantially equidistant from the eye.

12. The system of claim 1 further comprising a storage device configured to store the feedback communication.

13. The system of claim 1 further comprising a storage device configured to store the output from the detection device.

14. The system of claim 1, wherein the visual access for the eye comprises at least one portal contained in a wall of the enclosure.

15. The system of claim 1, wherein the enclosure is at least partially transparent.

16. An apparatus for detecting an electromagnetic field emanating via an eye, wherein the apparatus comprises:
   an enclosure containing a detection device comprising at least one electrode configured to produce an output corresponding to an electromagnetic field produced by a body and emanating from an eye of the body;
   wherein the detection device is a non-contacting electrode, wherein the non-contacting electrode detects the electromagnetic field without making substantial contact with a surface of the body; and
   an opening in the enclosure configured to establish a communication pathway between the eye and the detection device.

17. The apparatus of claim 16, further comprising:
   another electrode configured to produce an output corresponding to an electromagnetic field and removed from a line of sight of the at least one electrode; and
   a reflective member configured to establish a communication pathway between the eye and the other electrode via the reflective member.

18. The apparatus of claim 16, wherein the at least one electrode further comprises a plurality of electrodes configured to produce a plurality of output corresponding to an electromagnetic field and provided substantially equidistant from the eye when the eye is proximate to the opening.

19. The apparatus of claim 16, wherein the enclosure further contains an illuminating device.

20. The apparatus of claim 16, wherein the at least one electrode is a high input impedance electrode with an input impedance in the range of $10^7\Omega$ to $10^{15}\Omega$.

21. The apparatus of claim 16, wherein the enclosure is electromagnetically shielded.

22. A system for detecting an electromagnetic field comprising:
   an enclosure containing at least one portal configured to facilitate visual access for an eye of a body;
   at least one high input impedance electrode contained within the enclosure and configured to produce an output corresponding to an electromagnetic field produced by the body and emanating from the eye of the body with an input impedance in the range of $10^7\Omega$ to $10^{15}\Omega$;
   wherein the high input impedance electrode is a non-contacting electrode, wherein the non-contacting electrode detects the electromagnetic field without making substantial contact with a surface of the body;
   a processing device configured to receive the output from the electrode; and
   a communication device configured to provide feedback communication corresponding to the output from the electrode.

* * * * *